United States Patent
Hu

(10) Patent No.: US 9,850,200 B1
(45) Date of Patent: Dec. 26, 2017

(54) METHOD FOR PREPARING TAURINE

(71) Applicant: VITAWORKS IP, LLC, North Brunswick, NJ (US)

(72) Inventor: Songzhou Hu, Princeton, NJ (US)

(73) Assignee: VITAWORKS IP, LLC, North Brunswick, NJ (US)

( * ) Notice: Subject to any disclaimer, the term of this patent is extended or adjusted under 35 U.S.C. 154(b) by 0 days.

(21) Appl. No.: 15/366,783

(22) Filed: Dec. 1, 2016

(51) Int. Cl.
*C07C 303/02* (2006.01)
*C07C 303/32* (2006.01)
*C07C 303/44* (2006.01)

(52) U.S. Cl.
CPC .......... *C07C 303/02* (2013.01); *C07C 303/32* (2013.01); *C07C 303/44* (2013.01)

(58) Field of Classification Search
None
See application file for complete search history.

(56) References Cited

U.S. PATENT DOCUMENTS

| | | |
|---|---|---|
| 8,609,890 B1 | 12/2013 | Hu |
| 9,061,976 B1 | 6/2015 | Hu |
| 9,428,450 B2 | 8/2016 | Hu |
| 9,428,451 B2 | 8/2016 | Hu |
| 2014/0121405 A1 | 5/2014 | Chen |

*Primary Examiner* — Clinton Brooks
(74) *Attorney, Agent, or Firm* — Graham Curtin, P.A.

(57) ABSTRACT

There is disclosed a process for preparing taurine from alkali isethionate by reacting alkali taurinates in the solution of ammonolysis reaction of alkali isethionate with ammonium bisulfite or ammonium sulfite to obtain taurine and to regenerate alkali bisulfite or alkali sulfite, which is used to react with ethylene oxide to afford alkali isethionate.

7 Claims, 1 Drawing Sheet

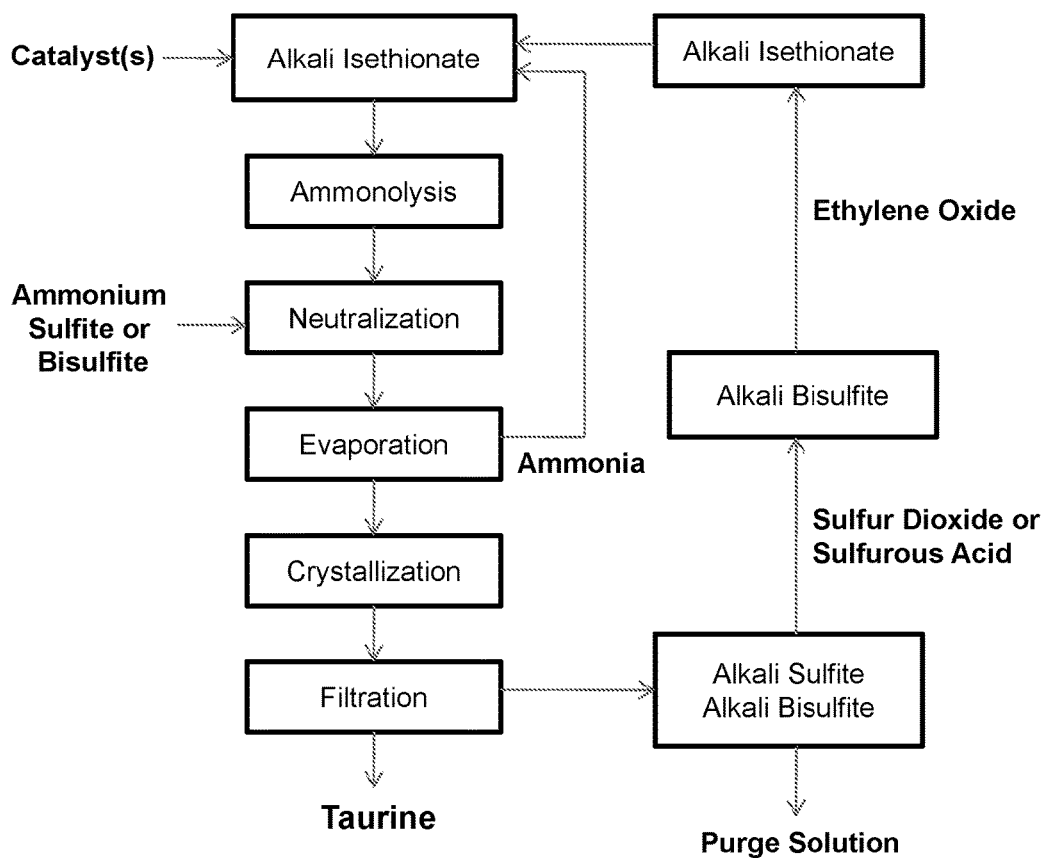

METHOD FOR PREPARING TAURINE

TECHNICAL FIELD

This invention relates to a method for preparing taurine from alkali isethionate in high yield which is economical and in which little waste is generated.

DESCRIPTION OF THE INVENTION

Taurine can be referred to as 2-aminoethylsulfonic acid and is of the formula $H_2NCH_2CH_2SO_3H$. Taurine is an extremely useful compound because it per se has such pharmacological effects as detoxification effect, fatigue-relieving effect and nourishing and tonifying effect. As a result, taurine finds wide applications as an essential ingredient for human and animal nutrition.

Many chemical synthetic methods have been known in the prior art for the preparation of taurine and related derivatives. The following two methods have been used in industry to manufacture over 60,000 tons of taurine per year, starting from ethylene oxide (the EO process) or monoethanolamine (the MEA process).

According to the EO process, ethylene oxide is reacted with sodium bisulfite to obtain sodium isethionate, which undergoes ammonolysis reaction to yield a mixture of sodium taurinate, sodium ditaurinate, and sodium tritaurinate. Neutralization with sulfuric acid yields a mixture of taurine, sodium sulfate, and sodium taurinates.

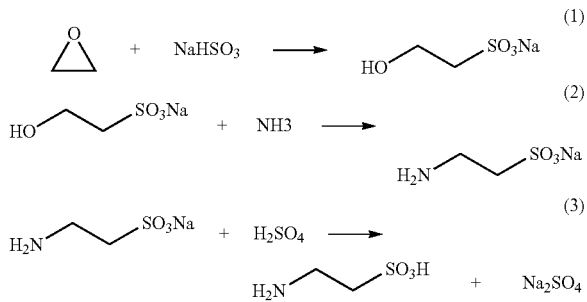

U.S. Pat. No. 9,428,450 and U.S. Pat. No. 9,428,451 significantly improve the current industrial process by converting the byproducts of the ammonolysis reaction, alkali ditaurinate and alkali tritaurinate, into alkali taurinate. As a result, the overall yield is increased to from 85% to nearly quantitative.

U.S. Pat. No. 8,609,890 discloses a cyclic process that using sulfur dioxide or sulfurous acid to neutralize alkali taurinate to regenerate alkali bisulfite according to the following reactions:

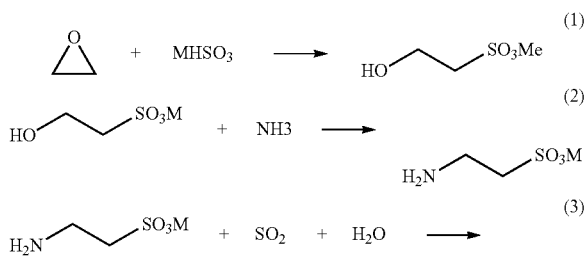
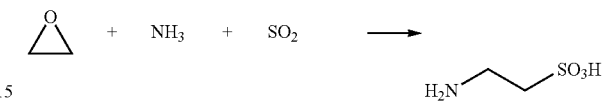

In the reactions, M stands for alkali metals, which can be lithium, sodium, and potassium.

U.S. Appl. No. 2014/0121405 describes a similar process for using sulfur dioxide to prepare taurine. The net reaction for the cyclic processes using sulfur dioxide as an acid is:

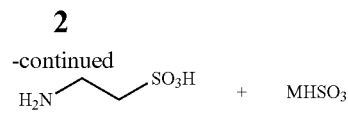

U.S. Pat. No. 9,061,976 further improves the process disclosed in U.S. Pat. No. 8,609,890 by converting the byproducts of the ammonolysis reaction, alkali ditaurinate and alkali tritaurinate, into alkali taurinate, thus achieving a very high overall yield without generating undesirable inorganic salt as byproduct.

In order to achieve the cyclic process, these prior art has used gaseous sulfur dioxide or sulfurous acid to neutralize alkali taurinate. However, the use of gaseous sulfur dioxide to neutralize alkali taurinate imparts a slight foul smell onto the final product, owing to the direct contact of sulfur dioxide with taurine.

It is an object of the present invention to overcome the disadvantages of the current process using gaseous sulfur dioxide. Specifically, the present invention discloses the use of an ammonium salt to react with alkali taurinate to obtain taurine and alkali salt. In particular, the present invention is related to the use of ammonium bisulfite, ammonium sulfite, or their mixture to react with alkali taurinates to yield taurine and to regenerate a mixture of alkali bisulfite and alkali sulfite. The reaction according to the present invention is described as following for the reaction of ammonium bisulfite with alkali taurinate:

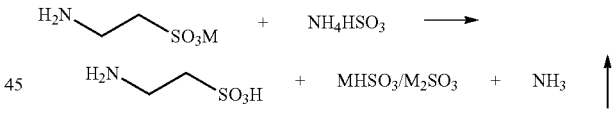

Other suitable ammonium salts are selected from the group of ammonium sulfate, ammonium bisulfate, ammonium chloride, ammonium bromide, ammonium nitrate, ammonium phosphate, ammonium carboxylate, ammonium alkyl sulfonate, or ammonium aryl sulfonate.

The process according to the present invention starts with the ammonolysis reaction of alkali isethionate, or its mixture with alkali ditaurinate and alkali tritaurinate in the presence of one or a combination of two or more catalysts to yield a mixture of predominantly alkali taurinate, alkali ditaurinate, and alkali tritaurinate, followed by the reaction of alkali taurinates with an ammonium salt, preferably with ammonium bisulfite, ammonium sulfite or their mixture. The process is schematically illustrated in FIG. 1 for a cyclic regeneration of alkali bisulfite and its subsequent reaction with ethylene oxide to produce the starting material of the process, alkali isethionate.

The ammonolysis reaction is carried out at a temperature from 160° C. to 280° C. under the pressure from autogenous to 260 bars for 1 to 6 hours.

Useful and effective catalysts are found among the alkali salts of hydroxide, carbonate, bicarbonate, hydrogen sulfate, sulfate, bisulfite, sulfite, nitrate, phosphate, chlorate, and perchlorate. Such salts are sodium hydroxide, lithium hydroxide, potassium hydroxide, lithium carbonate, lithium bicarbonate, sodium bicarbonate, sodium bicarbonate, potassium bicarbonate, lithium carbonate, sodium carbonate, potassium carbonate, lithium sulfate, sodium sulfate, potassium sulfate, lithium phosphate, sodium phosphate, potassium phosphate, lithium sulfite, sodium sulfite, and potassium sulfite.

The catalyst for the ammonolysis reaction of alkali isethionate or its mixture with alkali ditaurinate and alkali tritaurinate can be one component or a combination of two or more components. Preferable catalysts are alkali hydroxide and the most preferable catalyst is sodium hydroxide.

The amount of the catalyst used is not limited, but is usually from 0.01 to 10 in molar ratio of the catalyst to alkali isethionate. The ratio is preferably in the range of 0.01 to 1, more preferably 0.1 to 0.5, most preferably 0.2 to 0.3. A suitable amount of catalyst can be selected by those skilled in the art for the ammonolysis reaction to complete in desired time.

The amount of ammonium salt in relation to alkali taurinate in the ammonolysis solution can be from 0.1 to 10 on the molar basis. Preferably, the molar ratio is from 0.3 to 1.5, more preferably from 0.4 to 1.1, and most preferably from 0.45 to 1.05. When the ratio is lower than the equivalent, the final pH after ammonia removal tends to be higher than 7 and more taurine will remain in the solution. When the ratio is greater than equivalent, the final pH is in the desirable range of 6 to 7, but excess ammonium salt is consumed in the process.

As the excess ammonia and ammonia released from the reaction are removed from the solution by heating, the strongly basic solution becomes neutral in a range of pH 7-8, and a crystalline suspension of taurine is obtained upon concentrating and cooling in a solution of a mixture of alkali bisulfite and alkali sulfite. Taurine is recovered from the suspension by means of solid-liquid separation. Recrystallization from deionized water yields a product of pharmaceutical grade and shows no foul smell.

The mother liquor after the separation of taurine can be acidified with sulfur dioxide to regenerate alkali bisulfite, which can be reacted with ethylene oxide to obtain alkali isethionate. On the other hand, the mother liquor can also be concentrated to crystallize alkali metabisulfite or alkali sulfite if impurities have accumulated in the mother liquor to the extent that the cyclic process is interfered. The recovered alkali metabisulfite, alkali sulfite, or their mixture, which is now free of impurities, can then be used to react with sulfur dioxide to regenerate alkali bisulfite, which is reacted with ethylene oxide to form alkali isethionate to start the cyclic process.

The advantage of the cyclic process according to the present invention in comparison to the known process is that no acid nor base, which is foreign to the reaction system, is used. Consequently, the cost of acid and base is completely avoided.

In addition, no additional ammonia will be consumed in the process as the ammonia recovered from the reaction of alkali taurinate with ammonium bisulfite or ammonium sulfite is incorporated into taurine in subsequent ammonolysis reaction.

The process according to the present invention can be carried out discontinuously, semi-continuously, or continuously.

BRIEF DESCRIPTION OF THE DRAWING

FIG. 1 is a schematic flowchart for producing taurine from alkali isethionate.

EXAMPLES

The following examples will illustrate the practice of this invention but are not intended to limit its scope.

Example 1

To an one liter autoclave were added 600 mL of 24% ammonium hydroxide solution, 126 g of sodium isethionate, and 2.0 g of sodium hydroxide. The solution was heated to 250° C. for 2 hours. To the solution was added 160 g of 55% ammonium bisulfite. After complete removal of ammonia from the solution by heating, the pH of the solution became 7-8. After concentrating and cooling, 93 g of crystalline taurine was obtained by filtration in a yield of 74.4%.

Example 2

To an one liter autoclave were added 600 mL of 24% ammonium hydroxide solution, 126 g of sodium isethionate, and 2.0 g of sodium hydroxide. The solution was heated to 250° C. for 2 hours. To the solution was added 85 g of ammonium sulfite monohydrate. After complete removal of ammonia from the solution by heating, the pH of the solution became 7-8. After concentrating and cooling, 95 g of crystalline taurine was obtained by filtration in a yield of 76%.

Example 3

The procedure was carried out the same as with Example 2, but with 75 g of ammonium sulfite monohydrate. After removal of ammonia by boiling the solution to 103° C., the final pH was 7.6. After concentrating and cooling, 94 g of crystalline taurine was obtained by filtration in a yield of 75.2%.

Example 4

Sulfur dioxide was passed into the mother liquor of Example 1 until the pH of the solution became 3.5. Then 44 g of ethylene oxide was added slowly. The solution was diluted with aqueous ammonia to a volume of 550 mL and then saturated with ammonia. After adding 16 g of sodium hydroxide, the solution was subjected to the ammonolysis reaction at 250° C. for 2 hours. To the solution was added 95 g of ammonium sulfite monohydrate. After complete removal of ammonia from the solution by heating the solution to a temperature of 104° C., the pH of the solution became 7-8. After concentrating and cooling, 118 g of crystalline taurine was obtained by filtration in a yield of 94.4%.

Example 5

To an one liter autoclave were added 600 mL of 24% ammonium hydroxide solution, 126 g of sodium isethionate, and 2.0 g of sodium hydroxide. The solution was heated to 250° C. for 2 hours. To the solution was added 64 g of ammonium chloride. After complete removal of ammonia from the solution by heating, the pH of the solution became 7-8. After concentrating and cooling, 98 g of crystalline taurine was obtained by filtration in a yield of 78.4%.

It will be understood that the foregoing examples, explanation and drawing are for illustrative purposes only and that various modifications of the present invention will be self-evident to those skilled in the art. Such modifications are to be included within the spirit and purview of this application and the scope of the appended claims.

What is claimed is:

1. A process for producing taurine from alkali taurinate or a mixture of alkali taurinate, alkali ditaurinate, and alkali tritaurinate, comprising:
   (1) adding ammonium bisulfite, or ammonium sulfite, or their mixture to a solution of alkali taurinate or a mixture of alkali taurinate, alkali ditaurinate, and alkali tritaurinate to yield ammonium taurinate and a mixture of alkali sulfite and alkali bisulfite;
   (2) decomposing ammonium taurinate by heating and removing ammonia to yield taurine;
   (3) separating taurine by means of solid-liquid separation to provide a mother liquor containing a mixture of alkali sulfite and alkali bisulfite.

2. The process according to claim 1, wherein a mixture of alkali taurinate, alkali ditaurinate, and alkali tritaurinate is produced by an ammonolysis reaction of alkali isethionate or a mixture of alkali isethionate, alkali ditaurinate, and alkali tritaurinate.

3. The process according to claim 2, wherein a process for using the mother liquor to produce alkali isethionate comprises:
   (a) concentrating the mother liquor to crystallize alkali bisulfite, alkali metabisulfite, alkali sulfite, or their mixture and recovering the solid by means of solid-liquid separation;
   (b) dissolving alkali metabisulfite, alkali sulfite, or their mixture from step (a) in water and reacting the solution with sulfur dioxide or sulfurous acid to form a solution of alkali bisulfite;
   (c) adding ethylene oxide to the solution of step (b) to react with alkali bisulfite to form alkali isethionate.

4. The process according to claim 1, wherein the molar ratio of ammonium salt to alkali taurinates in the ammonolysis solution is from 0.1 to 10.

5. The process according to claim 1, wherein the molar ratio of ammonium salt to alkali taurinates in the ammonolysis solution is from 0.4 to 1.1.

6. The process according to claim 2, wherein a process for recycling the mother liquor to produce a solution of a mixture of alkali isethionate, alkali ditaurinate, and alkali tritaurinate, comprises:
   (a) reacting the mother liquor, containing a mixture of alkali sulfite and alkali bisulfite, with sulfur dioxide or sulfurous acid, to form alkali bisulfite;
   (b) adding ethylene oxide to the solution of step (a) to react with alkali bisulfite to form alkali isethionate in the presence of alkali ditaurinate and alkali tritaurinate.

7. The process according to claim 1, wherein the alkali metals are lithium, sodium, or potassium.

* * * * *